(12) United States Patent
Bainton et al.

(10) Patent No.: US 10,500,346 B2
(45) Date of Patent: Dec. 10, 2019

(54) ASSEMBLY FOR A DRUG DELIVERY DEVICE

(71) Applicant: Sanofi, Paris (FR)

(72) Inventors: Michael Bainton, Kineton Warwickshire (GB); David Aubrey Plumptre, Worcestershire (GB)

(73) Assignee: Sanofi, Paris (FR)

( * ) Notice: Subject to any disclaimer, the term of this patent is extended or adjusted under 35 U.S.C. 154(b) by 138 days.

(21) Appl. No.: 14/915,440

(22) PCT Filed: Sep. 3, 2014

(86) PCT No.: PCT/EP2014/068659
§ 371 (c)(1),
(2) Date: Feb. 29, 2016

(87) PCT Pub. No.: WO2015/032785
PCT Pub. Date: Mar. 12, 2015

(65) Prior Publication Data
US 2016/0367760 A1  Dec. 22, 2016

(30) Foreign Application Priority Data
Sep. 3, 2013 (EP) ..................................... 13182767

(51) Int. Cl.
*A61M 5/315* (2006.01)
*A61M 5/24* (2006.01)
*A61M 5/31* (2006.01)

(52) U.S. Cl.
CPC .......... *A61M 5/31553* (2013.01); *A61M 5/24* (2013.01); *A61M 5/31585* (2013.01);
(Continued)

(58) Field of Classification Search
CPC .. A61M 5/31553; A61M 5/3155; A61M 5/24; A61M 2005/3126; A61M 5/31585
See application file for complete search history.

(56) References Cited

U.S. PATENT DOCUMENTS 5,279,586 A * 1/1994 Balkwill ............. A61M 5/3158
222/309
5,921,966 A 7/1999 Bendek et al.
(Continued)

FOREIGN PATENT DOCUMENTS

CN   1509193    6/2004
CN   102711878  10/2012
(Continued)

OTHER PUBLICATIONS

International Search Report and Written Opinion in International Application No. PCT/EP2014/068659, dated Nov. 24, 2014, 10 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

An assembly for a drug delivery device includes a dose setting member to be moved by a user from an initial position to a dose sett position and a housing part. The dose setting member and the housing part are connected to form a housing of the assembly. The assembly includes an activation member coupled to the dose setting member to convert a rotation of the dose setting member with respect to the housing into a proximal movement of the activation member with respect to the dose setting member when the dose setting member is moved from the initial position to the dose set position. The activation member has a proximal end section extending from an activation face of the activation member, where in the initial position of the dose setting member, the proximal end section is fully in or slightly protrudes from the proximal end of the housing.

21 Claims, 7 Drawing Sheets
Specification includes a Sequence Listing.

(52) U.S. Cl.
CPC ............ *A61M 2005/3126* (2013.01); *A61M 2205/581* (2013.01); *A61M 2205/582* (2013.01); *A61M 2205/584* (2013.01); *A61M 2205/586* (2013.01)

(56) References Cited

U.S. PATENT DOCUMENTS

| | | | |
|---|---|---|---|
| 8,491,536 B2 * | 7/2013 | Giambattista | A61M 5/31553 604/186 |
| 2004/0019333 A1 | 1/2004 | Graf et al. | |
| 2015/0018777 A1 * | 1/2015 | Veasey | A61M 5/31528 604/211 |

FOREIGN PATENT DOCUMENTS

| | | |
|---|---|---|
| EP | 0498737 | 8/1992 |
| EP | 0897728 | 2/1999 |
| JP | H04-256757 | 9/1992 |
| JP | H11-104240 | 4/1999 |
| JP | 2005-532855 | 11/2005 |
| JP | 2012-502765 | 2/2012 |
| JP | 2013-513459 | 4/2013 |
| WO | WO 02/053214 | 7/2002 |
| WO | WO2008/058665 | 5/2008 |
| WO | WO 2010/033808 | 3/2010 |
| WO | WO2011/081867 | 7/2011 |

OTHER PUBLICATIONS

International Preliminary Report on Patentability in International Application No. PCT/EP2014/068659, dated Mar. 8, 2016, 8 pages.

* cited by examiner

000

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Pro Ser
    35

ASSEMBLY FOR A DRUG DELIVERY DEVICE

CROSS-REFERENCE TO RELATED APPLICATIONS

This application is a U.S. national stage application under 35 USC § 371 of International Application No. PCT/EP2014/068659, filed on Sep. 3, 2014, which claims priority to European Patent Application No. 13182767.7, filed on Sep. 3, 2013, the entire contents of which are incorporated herein by reference.

The present disclosure relates to an assembly for a drug delivery device and a drug delivery device, e.g. an injector-type device and/or a pen-type device.

A drug delivery device is, for example, known from WO 2008/058665 A1.

It is an object of the present disclosure to provide an assembly of one or more components which facilitate an improvement of a drug delivery device.

This object is achieved by the subject-matter of the independent claim. Advantageous embodiments and refinements are subject-matter of the dependent claims.

One aspect of the present disclosure relates to an assembly for a drug delivery device. The assembly comprises a dose setting member provided to be manipulated, particularly moved, by a user from an initial position to a dose setting position to set a dose. This movement may take place during a dose setting operation of the assembly. The dose setting operation may be an operation, wherein a size of a dose to be dispensed by the drug delivery device can be set. The assembly further comprises a main housing part, wherein the dose setting member and the main housing part are connected to form a housing of the assembly. The housing has a proximal end and a distal end.

The "distal end" of the drug delivery device or a component of the drug delivery device shall mean the end which is closest to the dispensing end of the drug delivery device. The "proximal end" of the drug delivery device or a component of the drug delivery device shall mean the end which is furthest away from the dispensing end of the drug delivery device.

The assembly further comprises an activation member. The activation member is coupled to the dose setting member to convert a rotation of the dose setting member with respect to the housing into a proximal movement of the activation member with respect to the dose setting member when the dose setting member is moved from the initial position to the dose set position. The activation member has a proximal end section extending from an activation face of the activation member. Particularly, side faces of the proximal end section of the activation member extend from the activation face. The activation face is provided for an interaction with the user. The assembly is configured such that in the initial position of the dose setting member, the proximal end section of the activation member is fully received in the housing or slightly protrudes by a protruding distance beyond the proximal end of the housing. Particularly, the side faces of the proximal end section of the activation member may be fully received in the housing or slightly protrude by a protruding distance beyond the proximal end of the housing. The assembly or the drug delivery device is, preferably configured such that, when the set dose is increased, the axial extension of the device also increases in proportion, as the activation member moves proximally with respect to the dose setting member or the housing. The assembly or the device may further be configured such that the activation member performs a helical travel during setting of a dose. The axial movement of an activation member during setting of a dose of the drug delivery device is, preferably, proportional to the number of units indicated by an indication mechanism.

As an advantage, the assembly may be embodied such that, during dispensing of a dose, the dose setting member or a gripping face thereof may be gripped by the user. This is possible because the dose setting member is part of the housing and preferably, does not move during dispensing of a dose with respect to the main housing part. In this way, the protruding distance between the activation face and the housing can, advantageously, be reduced in comparison to an assembly, wherein the axial extension of the dose setting member is added to the distance between activation face and the housing, e.g. if the dose setting member travels together with the activation face during dose setting. In this case the dose setting member is not a part of the housing.

Preferably, the user operates the assembly, particularly dispenses a dose of drug from the device by means of one hand. The thumb of the user, thereby, preferably contacts the activation face while the remaining fingers at least partly contact the housing, particularly, the dose setting member. The reduction of said distance, in turn, also reduces the distance the thumb of the user has to be stretched in order to contact the activation face. In this way, ergonomic handling of the assembly and/or the drug delivery device may be significantly improved.

The assembly and/or the device can, advantageously, be configured such that the protruding distance is small or, preferably, zero when the dose setting member is in the initial position.

In an embodiment, the proximal end section of the activation member comprises a colour indicating dose information.

Preferably, the activation face is a proximal end face of the activation member. A proximal end of the activation member may, thereby, be part of or lie in the activation face. The activation face may be configured to ergonomically match the shape of the user's thumb in order to ease operability of the assembly or the drug delivery device.

One aspect of the present disclosure relates to a drug delivery device comprising the assembly. The drug delivery device may further comprise a drive mechanism. The drive mechanism may comprise a drive member. The drive member may be coupled to a piston rod. The piston rod may be coupled to a piston or bung which may, in turn, be arranged in a cartridge containing a drug. The drive mechanism may be configured to be operable to dispense a dose of drug or to contribute to a dispensing operation of the drug delivery device. The drug delivery device comprises a longitudinal axis which, preferably, coincides with the longitudinal axis of the housing.

The drug delivery device may be a disposable device. Alternatively, the drug delivery device may be a reusable device.

In a preferred embodiment, the drug delivery device comprises a piston rod of the drive mechanism, the piston rod being configured symmetrically with respect to a vertical axis of the device or with respect to an axis which extends orthogonal to the longitudinal axis. According to this embodiment, an easy assembly of the piston rod to remaining parts of the assembly or the drug delivery device may be facilitated, as a feed of the piston rod through further components of the assembly, e.g. during an automated assembly, is eased. This is because the piston rod can be assembled in either direction of longitudinal alignment, thereby still functioning properly.

The initial position of the dose setting member may relate to a position in which a drug has not yet been set by the user. The initial position may relate to an as-assembled state of the assembly or the drug delivery device and/or to a position after a dose delivering action has been completed. The initial position may relate to a zero dose position, wherein no dose or a dose of zero units is set.

The dose set position of the dose setting member, preferably, relates to a position in which a dose of drug has been set by the user.

In the initial position of the dose setting member, the proximal end section of the activation member is, preferably fully received or accommodated in the housing such that it does not protrude beyond an outer surface of the housing or a contour thereof.

For delivering a dose, the user may have to push or press the activation member via the activation face in the distal direction with respect to the dose setting member when the dose setting member is in the dose set position. At the end of this dose setting operation, the proximal end section of the activation member is, preferably, again fully received in the housing or slightly protruding by the protruding distance beyond the proximal end of the housing.

In a preferred embodiment, the protruding distance is less than the axial length of the dose setting member. As an advantage, the protruding distance and/or the axial extension of the activation member from the housing may be kept small.

In an embodiment, the assembly is configured such that, during setting of the dose, the length of the activation member protruding beyond the proximal end of the housing, increases.

The embodiment, that the protruding distance and/or the axial extension of the activation member from the housing is kept small during an operation of the same, provides the advantage that a set dose can easily be dispensed by the user, as the activation member is more easily actuatable when the device is operated by the user with a single hand, as mentioned above.

Preferably, the drug delivery device is a manually driven device, wherein a set dose can be dispensed by the user by utilizing only one hand. The drug delivery device is preferably a non-automatic device. The drug delivery device is, furthermore, preferably, a user-settable device.

Preferably, an outer surface of the housing and the activation face are configured such that said components ergonomically match the human hand to facilitate comfortable operation of the device.

In an embodiment, the protruding distance is less than or equal to 20%, preferably less than or equal to 10%, more preferably less than or equal to 5%, of the maximum axial distance by which the activation member can be moved proximally with respect to the dose setting member during a dose setting operation.

In an embodiment, the protruding distance is less than 5 mm.

In an embodiment, the protruding distance is less than 2 mm, preferably less than 1 mm.

In an embodiment, the protruding distance is zero.

The protruding distance, preferably, relates to the distance between a proximal end of the activation member and a proximal end of the housing.

The protruding distance may also be negative, i.e. when the proximal end of the housing protrudes beyond the proximal end section of the activation member.

In an embodiment, the dose setting member is axially secured to but rotatable with respect to the main housing part. This embodiment provides the advantage that an outer surface of the dose setting member may provide the above mentioned gripping face, which may be gripped by the user during dispensing of a dose of drug. As mentioned above, thereby, the extension of the user's thumb by which he may actuate the dispensing operation may be reduced and the ergonomic handling of the assembly and/or the device may be improved. The housing of the assembly may be a housing of the drug delivery device.

The rotatable embodiment of the dose setting member with respect to the main housing part provides the advantage that, during setting of a dose, the dose setting member may be rotated with respect to the main housing part, whereby a dose setting operation of the device may be easily enabled or carried out. Particularly, the movement from the initial position to the dose set position may involve or be a rotational movement of the dose setting member.

In an embodiment, the activation member is rotationally locked with respect to a drive member of the assembly or the drug delivery device. As an advantage of this embodiment, the activation member may also support further functions of the assembly or the drug delivery device. The drive member may contribute to a dispensing operation of the drug delivery device in that it drives the piston rod, preferably in the distal direction in order to dispense a dose of drug from the device.

In an embodiment, the activation member is rotationally locked with respect to the dose setting member. This provides the advantage that a rotation of the dose setting member with respect to the main housing part may be transferred to the activation member.

In an embodiment, the assembly is configured such that a rotation of the activation member may at least partly be converted into an axial movement of the activation member with respect to the dose setting member. This may, for example, be achieved by a coupling of the activation member with respect to a further component which is, in turn, threadedly engaged with the housing or a component thereof.

In an embodiment, the activation member is coupled to a piston rod of the assembly such that the activation member is moved proximally with respect to the dose setting member when the dose setting member is moved from the initial position to the dose set position. Preferably, the activation member is coupled to the piston rod of the assembly via the drive member. When the dose setting member is moved from the initial position to the dose set position, the piston rod is, preferably, axially constrained with respect to the housing.

In an embodiment, the dose setting member has a sleeve-like shape. This embodiment may facilitate manipulation of the dose setting member by the user, e.g. during setting of the dose.

The assembly or the drug delivery device may be configured such that the user can manually operate the dose setting member during setting of a dose. Setting of a dose may relate to an increase of the dose when the dose setting member is in the initial position or to an increase or decrease of a dose when the dose setting member is in the dose set position.

In an embodiment, the dose setting member defines the proximal end of the housing. According to this embodiment, an operation of the assembly or the drug delivery device may be facilitated, as the user may e.g. grasp the housing with one hand in a more distal section and manipulate the dose setting member in the proximal section with the other hand.

An outer contour of the proximal end section of the activation member may be geometrically similar to an inner contour of a proximal end section of the dose setting member. Furthermore, the activation face or a contour of the activation face may be geometrically similar to a proximal end face of the housing.

In an embodiment, in the initial position of the dose setting member, the proximal end of the housing ends flush with the activation face. Thereby, the proximal end of the housing ends preferably flush with a point or a site being arranged in the activation face. According to this embodiment, an axial length of the drug delivery device may be optimized, i.e. minimized, as the protruding distance is zero.

In an embodiment, at least a portion of the dose setting member comprises a non-circular cross-section. Said portion may be an axial portion. This embodiment, advantageously, aids the user in rotating the dose setting member with respect to the main housing part, e.g. during a dose setting operation.

In an embodiment, the dose setting member further comprises a gripping feature, such as at least one projection projecting from an outer surface of the dose setting member. According to this embodiment, rotation of the dose setting member during setting of a dose can be assisted.

The dose setting member may further comprise a portion, preferably an axial portion with a circular cross-section.

The non-circular portion may proximally follow the circular portion such that the user may grasp and rotate the dose setting member at its proximal end, e.g. to set a dose.

In an alternative embodiment, the cross-section of the dose setting member may be fully circular. According to this embodiment, the cross-section of the dose setting member, preferably increases towards a distal end of the dose setting member such that, e.g., a rotation of the dose setting member during setting of a dose is eased or facilitated by the increased cross-sectional diameter of the dose setting member.

In an embodiment, the activation face is curved. Preferably, the activation face is curved such that it ergonomically matches to the surface of the user's thumb. To this effect, the activation face may be concave. According to this embodiment, an ergonomic handling of the device, particularly depressing of the activation member during a dispense operation, is facilitated.

In an embodiment, the drug delivery device comprises a needle or a needle assembly. Through said needle or needle assembly, a drug or medical substance which may be retained in a cartridge of the device, can be dispensed from the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous of the subject matter of the disclosure will become apparent from the following description of the exemplary embodiment in conjunction with the figures, in which:

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 1:
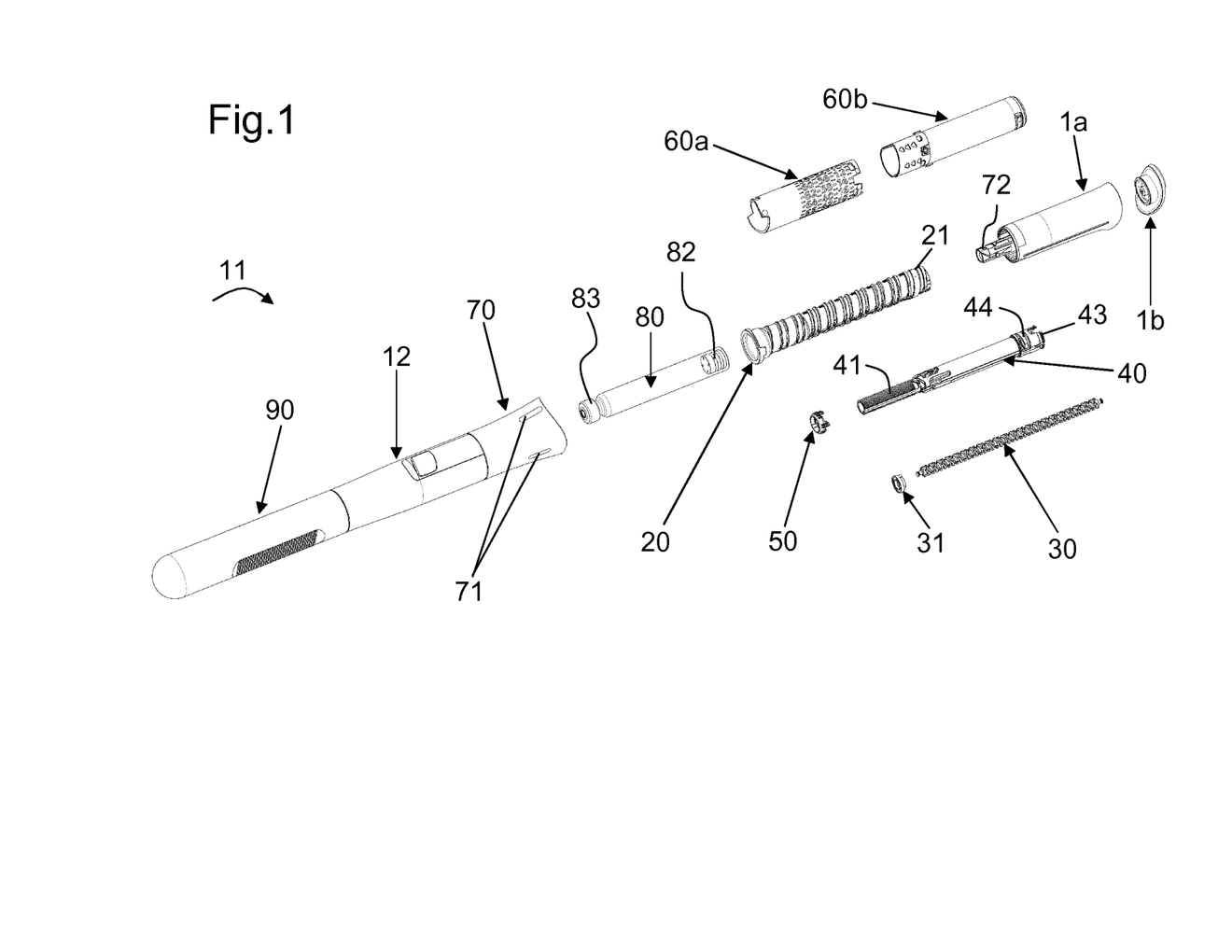
FIG. 1 shows an exploded view of components of a drug delivery device.

FIG. 1 shows a housing 11 of the drug delivery device 100 in the form of an injection pen. In an assembled state, the housing 11 may house or accommodate further components of the drug delivery device 100 such that a distal and a proximal end of the housing 11 correspond to a distal end 16 and the proximal end 17 of the drug delivery device 100, respectively (cf. numerals 16, 17 in FIG. 2). Further components of the drug delivery device 100 are shown on the right in FIG. 1.

The drug delivery device 100 comprises a housing part 12, an inner body 20, a piston rod 30, a driver 40, a nut 50, a dose setting member 70, an activation member 1, a cartridge 80 and a cap 90.

The housing 11 of the drug delivery device may be formed by the housing part 12, the cap 90 and the dose setting member 70. The dose setting member 70 is a component separate from the housing part 12. Preferably, the dose setting member 70 is connected to the housing part 12 such that the dose setting member 70 is axially constrained but rotatable with respect to the housing part 12. The dose setting member 70 comprises a proximal portion 4 with a non-circular cross-section.

The drug delivery device 100 further comprises a distal indication member part 60a and a proximal indication member part 60b. Said indication member parts are preferably rigidly connected to each other when the drug delivery device 100 is in an assembled state. To this effect, in the following, it is referred to as indication member 60, whereby an indication member consisting of the distal part 60a and the proximal part 60b is meant.

The drug delivery device 100 further comprises a main activation member part 1a and an activation member button 1b. The main activation member part 1a and the activation member button 1b are preferably rigidly connected to each other when the drug delivery device 100 is in an assembled state. To this effect, in the following, it is referred to an activation member 1, whereby an activation member consisting of the main activation member part 1a and the activation member button 1b is meant.

A needle arrangement comprising a needle hub and a needle cover (not shown) may be provided as additional components.

The housing part 12 is a generally tubular element which may form a cartridge holder for receiving cartridge 80 at its distal end. In a preferred embodiment, the housing part 12 is transparent. The housing part may further be provided with an opaque layer (cf. numeral 13 in FIG. 3). Preferably, the opaque layer 13 covers most of the housing part 12 with the exception of a transparent window 14. A main housing part may be the housing part 12.

Figure 2:
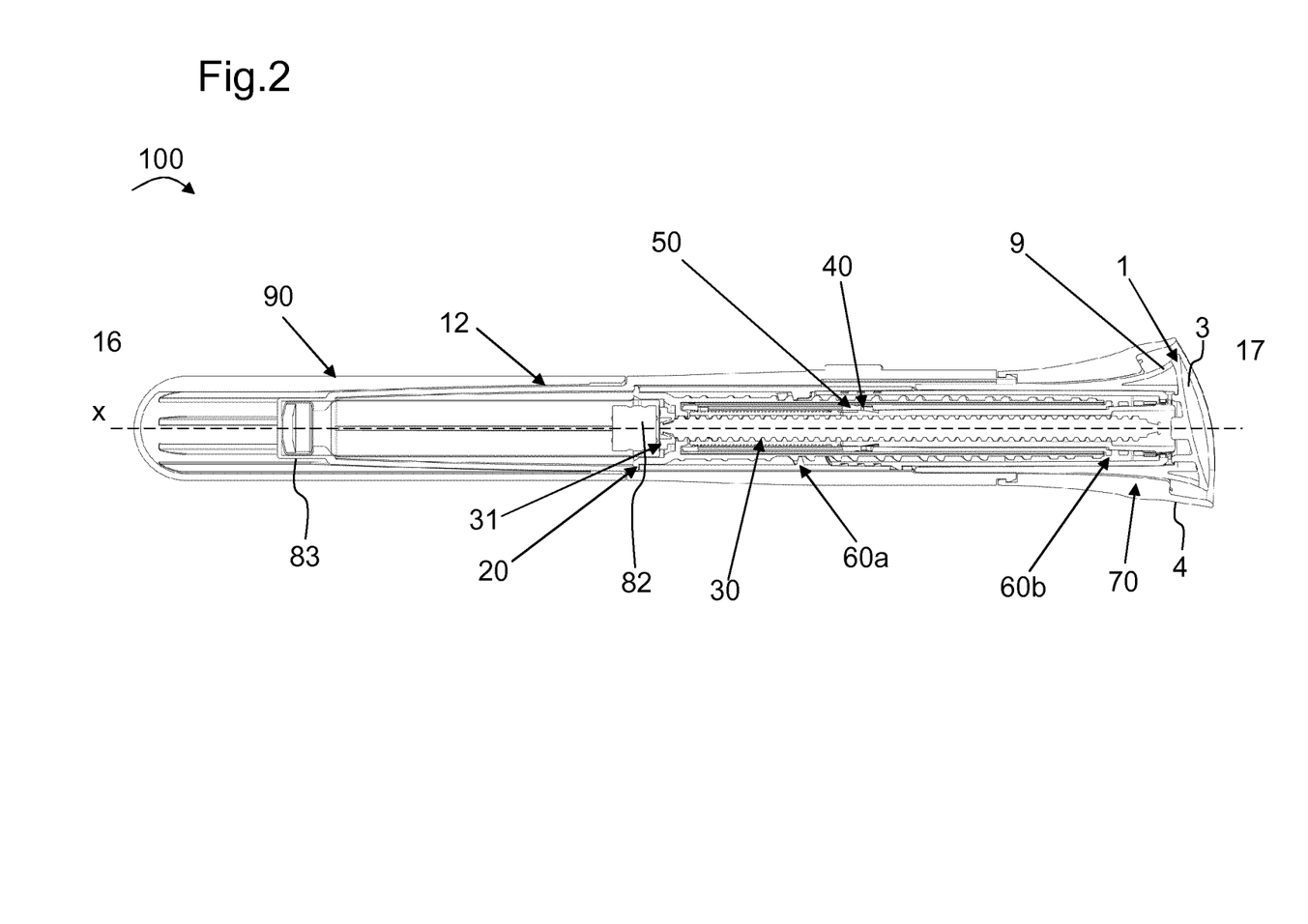
FIG. 2 shows a longitudinal section view of the drug delivery device.

The inner body 20 is a generally tubular element. As can be seen in FIG. 2, for instance, the inner body 20 is received in the housing part 12 and permanently fixed therein to prevent any relative movement of the inner body 20 with respect to the housing part 12. An external thread 21 is provided on the outer surface of the inner body 20.

When referring to an inner housing, it may also be referred to the inner body. As the same component is meant, the same reference numerals are used for the inner housing and the inner body. The inner housing or the inner housing part may be the inner body.

The piston rod 30 is an elongate element which may have two external threads or thread features (not explicitly indicated). One of these threads may engage an inner thread of the inner body 20. The piston rod may be embodied symmetrically with respect to an axis which is orthogonal to the longitudinal axis (cf. x in FIG. 2), such as a vertical axis. Thereby, a more simple insertion or assembly of the piston rod in or in collaboration with further components of the drug delivery device may be facilitated, because the piston rod can be assembled in either orientation.

The drug delivery device 100 further comprises a bearing 31 which is configured to interact with the piston rod 30.

The driver 40 is a generally tubular element having different diameter regions. When referring to a drive member, it may also be referred to the driver. As the same component is meant, the same reference numerals are used for the drive member and the driver. The drive member may be the driver.

A distal region of the driver 40 has an external thread 41. An inner surface of the driver 40 has an inner thread (not explicitly shown) engaging the thread of the piston rod not engaging the inner thread of the inner body 20. The driver 40 surrounds the piston rod 30 and is at least partly located within inner body 20. The driver 40 has at least one proximal opening 43. Further, at least one flexibly hinged protrusion 45 (cf. FIG. 5) is provided on the driver 40 by a cut-out in a wall of the driver 40. The protrusion 45 is allowed to flex radially inwardly. Protrusion 45 engages splines 22 (cf. FIG. 5) of the inner body 20.

The nut 50 is provided between the inner body 20 and the driver 40. When referring to a last dose member, it may also be referred to as the nut. As the same component is meant, the same reference numerals are used for the nut and the last dose member. The last dose member may be the nut.

Figure 5:
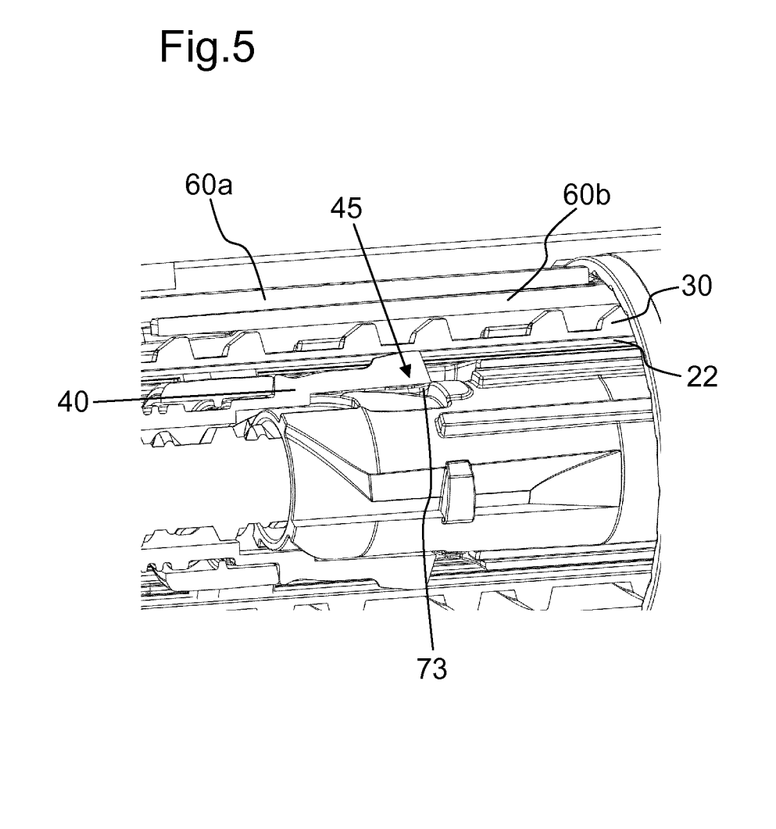
FIG. 5 shows a partial perspective view of inner components of the drug delivery device, illustrating a feedback mechanism.

External ribs (not explicitly indicated) of the nut 50 also engage the splines 22 of the inner body 20. An internal thread (not explicitly indicated) of the nut engages the external thread 41 of the driver 40. As an alternative, splines and ribs could be provided on the interface between the nut 50 and the driver 40 and threads could be provided on the interface between the nut 50 and the inner body 20. As a further alternative, the nut 50 may be designed as e.g. a half nut. Further, four rotational hard stops (not explicitly indicated) may be provided on nut 50 for interaction with corresponding stops (not explicitly indicated) on the driver 40 at the proximal end of thread 41.

The indication member 60 is a generally tubular element with an internal thread engaging the external thread 21 of the inner body 20. Thus, the indication member 60 is interposed between the inner body 20 and the housing part 12. A series of numbers (not shown) may be provided, e.g. printed, on the outer surface of the indication member 60. The numbers may be arranged on a helical line such that only one number or only a few numbers are visible through window 14 (cf. FIG. 3) of the housing part 12. As will be explained in more detail below, the indication member 60 is attached to the driver 40 preventing relative axial movement but allowing relative rotation.

The activation member 1 comprises a proximal end section 9 with a non-circular cross-section comparable to the proximal section 4 of the dose setting member 70. The activation member 1 further comprises an activation face 3 which is provided for an interaction with a user. The proximal end section 9 extends from an activation face 3 of the activation member 1.

The dose setting member further comprises a gripping face 5 which may be gripped by the user during an operation of the drug delivery device 100. Accordingly, the distance between the activation face 3 and the housing 11 (cf. FIG. 6) can, advantageously, be reduced as compared to an assembly, wherein the axial extension of the dose setting member is added to the distance between activation face and gripping face of the housing, e.g. if the dose setting member travels together with the activation face during dose setting. In this case the dose setting member is not a part of the housing. The reduction of said distance, in turn, also reduces the distance the thumb of the user has to be stretched in order to contact the activation face 3. In this way, ergonomic handling of the assembly and/or the drug delivery device 100 may be significantly improved.

A sleeve-like part 72 of the activation member 1 with a reduced diameter extends in the distal direction and is inserted into the driver 40 such that a limited relative axial movement is allowed but relative rotation is prevented. A recess 73 (cf. FIG. 5) which generally has the outline of the protrusion 45 is provided in the sleeve-like part 72 of activation member 1.

Figure 4:
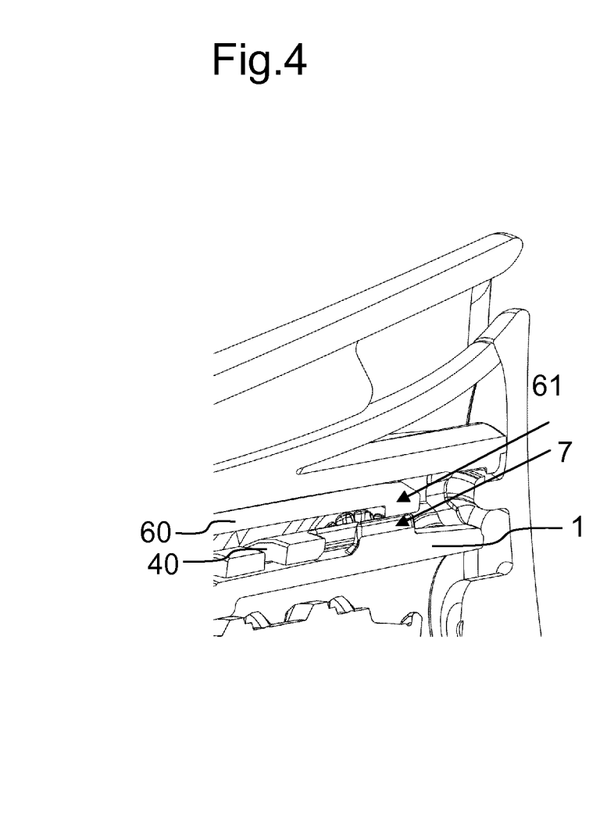
FIG. 4 shows a partial perspective view of inner components of the drug delivery device, illustrating a clutch between an indication member and a drive member.
Figure 7:
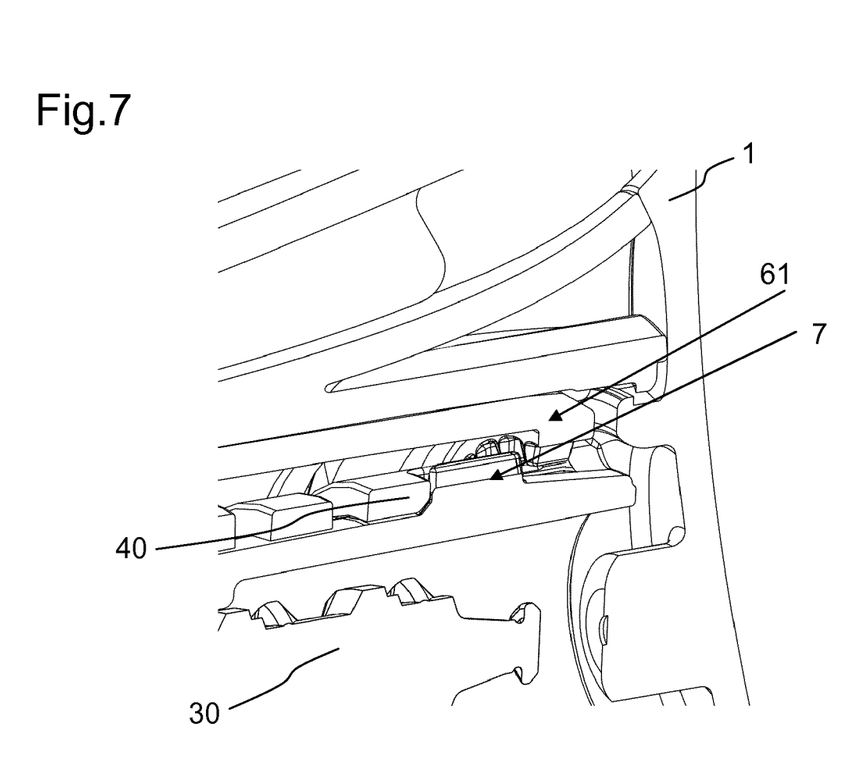
FIG. 7 shows a partial perspective view of inner components of the drug delivery device comparable to FIG. 4 in which the clutch between the indication member and the drive member is disengaged.

A clutch is provided between the indication member 60 and the activation member 1 by corresponding teeth 61 and 7 of the indication member 60 and the activation member 1, respectively (cf. FIGS. 4 and 7). If said teeth engage with each other, the indication member 60 and the activation member 1 are rotationally locked with respect to each other. A resilient finger 44 of the driver 40 biases the activation member 1 in the proximal direction of the device 100, i.e. in a direction engaging the clutch teeth. The clutch can be released allowing relative rotation by shifting the activation member 1 axially with respect to the indication member 60 against the bias of finger 44.

The cartridge 80 includes a pre-filled, necked-down cartridge reservoir which may be typically made of glass. A rubber type bung 82 or stopper is located at the proximal end of the cartridge reservoir and a pierceable rubber seal (not shown) is located at the other, distal, end. A crimped annular metal band 83 is used to hold the rubber seal in place. The cartridge 80 is provided within the cartridge holder of the housing part 12 with bearing 31 of piston rod 30 abutting bung 82. The bung 82 may be a piston. The cartridge may contain a number of units or other sub-quantities of drug.

FIG. 1 shows the cap 90 attached to the distal end 16 of the device 100, thus covering the cartridge holder. The cap 90 may be releasably snapped onto the housing part 12 and can be taken off for use of the device 100.

The components shown right in FIG. 1 may have a longitudinal axis which coincides with a longitudinal axis x (cf. FIG. 2) of the housing 11 or the drug delivery device 100. When the device is assembled, said components may be concentrically arranged within or retained by the housing 11.

In FIG. 2, the drug delivery device 100 is shown in an as-assembled state, i.e. in a state in which no dose has been dispensed. Said state may relate to a situation in which a user has not yet operated or manipulated the drug delivery device 100 by any means but in which the device is just delivered to the user. In FIG. 2, it is shown that the activation member 1 is completely received in the proximal end of the housing 11. In this situation, the dose setting member 70 is in an initial position.

The activation member 1 comprises an activation face 3 which may form a proximal end face of the activation member 1. The activation face 3 is provided to be manipulated by the user, preferably during a dose dispensing operation.

The housing part 12, the dose setting member 70 and the activation member 1 may form or belong to an assembly of the drug delivery device 100.

Figure 3:
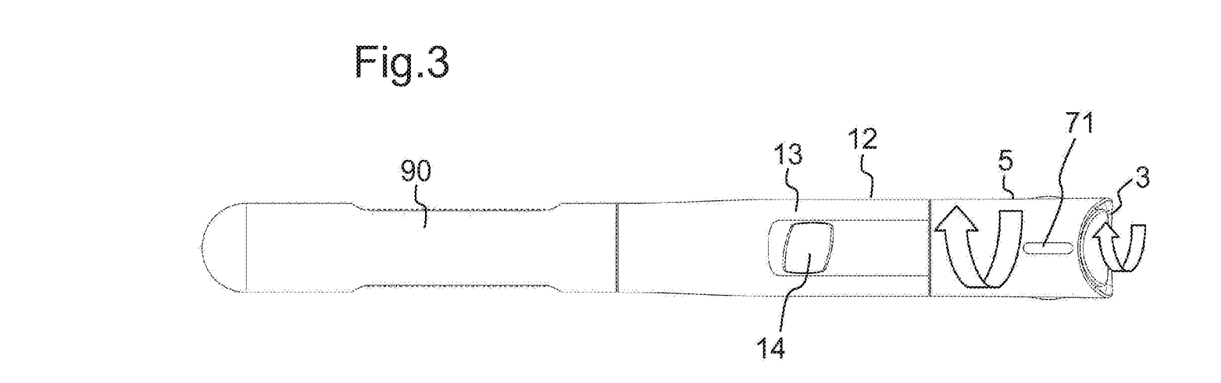
FIG. 3 shows a longitudinal view of the drug delivery device.

FIG. 3 shows a proximal end of the drug delivery device 100 in which the device has been rotated by 90° with respect to the illustration shown in FIG. 2. From this perspective, the drug delivery device 100 or at least a proximal end thereof, appears with a homogeneous width or diameter. The dose setting member 70 further comprises gripping features 71. The gripping features 71 are provisioned to assist a rotation of the dose setting member 70 by the user, e.g. during setting of a dose of drug. For setting of a dose, the dose setting member 70 is, preferably, rotated by the user. It can also be further gathered from FIG. 3 that the activation face 3 is curved such that it ergonomically matches to a finger, e.g. a thumb, of the user. To this effect, the activation face may be tilted, such that a central surface normal of the activation face 3 deviates from the longitudinal direction. Thereby, an easy operation of the drug delivery device, especially a dose dispensing operation is facilitated. Similar to the curvature of the activation face 3, the dose setting member 70 may also have a curvature at its proximal end.

Figure 9:
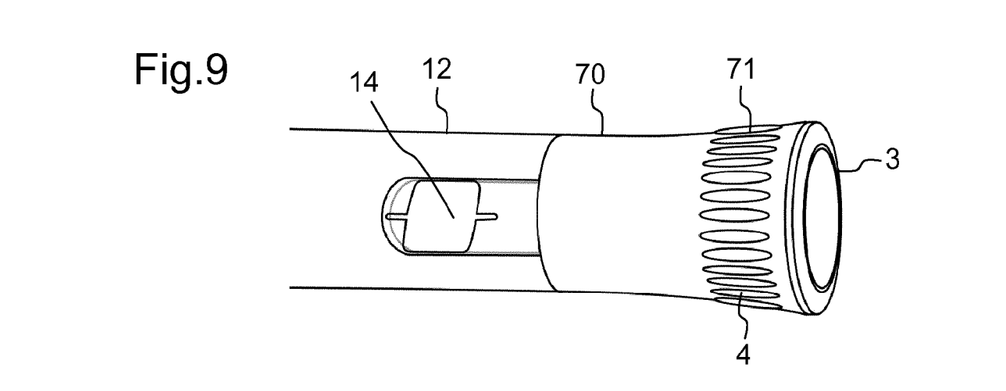
FIG. 9 shows a proximal end of the drug delivery device according to an alternative embodiment.

In FIG. 3, it is shown that the activation face 3 may end flush with a proximal end face of the dose setting member 70 such that the protruding distance, by which the activation member 1 protrudes beyond the proximal end of the housing is zero (cf. also FIG. 9).

FIG. 4 illustrates a clutch mechanism between the indication member 60 and the drive member 40 via the activation member 1. In FIG. 4, said clutch mechanism is engaged.

The indication member 60 comprises an indication clutch feature 61 which is configured to interact with an activation clutch feature 7 such that the indication member 60 is rotationally locked with respect to the activation member 1. When the drug delivery device 100 is in a dose set position and the user presses the activation member 1 distally to dispense a dose, the activation clutch feature 7 is moved out of engagement with the indication clutch feature 61 such that, during dispensing of a dose, the indication member 60 is rotatable with respect to the activation member 1 (cf. FIG. 7).

During dose setting, the dose setting member 70, activation member 1, driver 40 and indication member 60 are rotationally locked together via the clutch features 7 and 61. Further, the activation member 1, driver 40 and indication member 60 are axially coupled. Thus, these three components wind out of the housing 11 during dose setting. As a result, during dose setting, rotation of the dose setting member 70 in a clockwise fashion causes the indication member 60, activation member 1 and driver 40 to wind out of the device 100, due to the threaded engagement between the indication member 60 and the inner body 20.

As described above, clockwise rotation of the dose setting member 70 during dose setting causes the driver 40 to rotate on a helical path and, in doing so, it advances along the thread of the piston rod 30, which remains fixed throughout setting or dialling.

FIG. 5 shows the protrusion 45 and splines 22 forming a clicker arrangement that provides tactile and audible feedback to the user when dialling doses. This clicker arrangement has the further functions of defining discrete positions for the indication member 60 when dialling and of providing a method of locking the rotation of the driver 40 and hence activation member 1 when dosing or dispensing.

During dialling (dose setting) the activation member 1 is in an axial position relative to the driver 40 such that the pocket or recess 73 is located radially inwards of the protrusion 45. Thus, the protrusion 45 is allowed to flex radially inwards to overcome splines 22, thereby providing a tactile and audible feedback to the user (cf. FIG. 5).

The last dose member or nut 50 provides the function of counting the number of dispensed units. The nut 50 locks the dose setting member 70 at the end of life and as such no more drug can be dialled or dispensed by the user. The last dose nut 50 and the driver 40 are connected via a threaded interface, as explained above. Further, the last dose nut 50 is assembled into splines 22 (cf. FIG. 5) such that the nut 50 and the inner body 20 are rotationally locked together. Rotation of the driver 40 during dialling causes the nut 50 to advance along the driver thread 41. The nut 50 is free to slide axially within the inner body 20 at all times which allows advancement of the nut 50.

Figure 6:
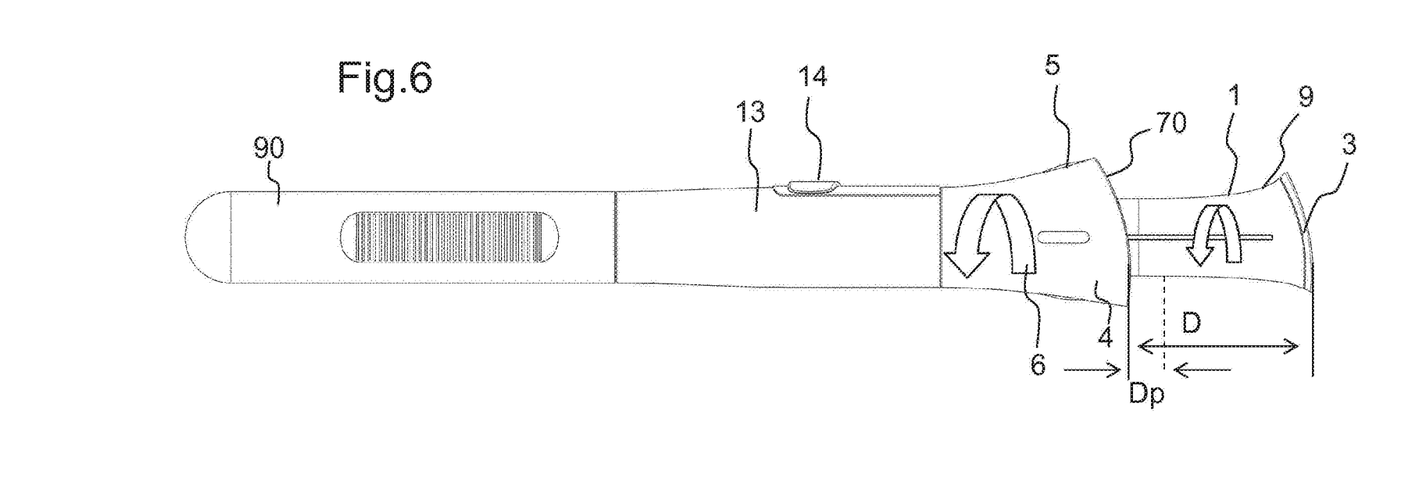
FIG. 6 shows a side view of a proximal end of the drug delivery device in a state in which a dose is set.

FIG. 6 shows the proximal end of the drug delivery device 100 in a state in which a dose, e.g. a maximum dose of drug, is set. The distance D is the maximum axial distance (cf. FIG. 6) by which the activation member 1 can be moved proximally with respect to the dose setting member 70 during a dose setting operation. In contrast to FIG. 3, in FIG. 6, the activation member 1 is in a dose set position, wherein the activation member 1 protrudes by the distance D beyond the proximal end of the housing 11, particularly beyond the dose setting member 70.

The protruding distance is indicated with Dp in FIG. 6, referring to an initial position of the dose setting member, e.g. to a position, wherein no dose is set. Thereby, the activation member 1 slightly protrudes by the protruding distance Dp beyond the proximal end of the housing. The protruding distance is favourably as small as possible. Preferably, the protruding distance is zero.

Preferably, the drug delivery device 100 is configured such that the activation member 1 can be moved from the initial position to the dose set position when the user rotates the dose setting member 70 with respect to the housing part 12. Thereby, the activation member 1 is moved proximally with respect to the dose setting member 70. The user may thereby, e.g. grip the housing part 12 with one hand and rotate the dose setting member 70 with the other hand. Said relative rotation of the housing part 12 and the dose setting member 70 is eased by the non-circular cross section of the proximal section 4 of the dose setting member 70. Said rotation may relate to a clockwise rotation of the dose setting member 70 with respect to the housing part 12.

Said rotation may relate to a dose setting operation of the drug delivery device 100. A dose setting operation, preferably, comprises the increasing of a dose such that an increased number of dose units or quantities is displayed though the window 14 but could also be the decreasing or cancelling of a previously set dose.

The activation member 1 is rotationally locked with respect to the dose setting member 70 such that, when a user rotates the dose setting member 70, the activation member 1 also rotates with respect to the housing part 12.

In FIG. 6, the activation member 1 protrudes by an axial distance D beyond the proximal end of the housing 11, particularly beyond the dose setting member 70. It is shown that the contours of the proximal section 4 of the dose setting member and the proximal end section 9 of the activation member 1 are substantially geometrically similar. This configuration allows a guidance of the activation member 1 by the dose setting member 70 when the activation member 1 is moved distally again with respect to the dose setting member 70 such that the activation member 1 is received by the dose setting member 70. With the desired dose dialled, the device 100 is ready for dose dispensing. This requires pushing of the activation member 1, which will result in a disengagement of the clutch features 61,7.

Figure 8:
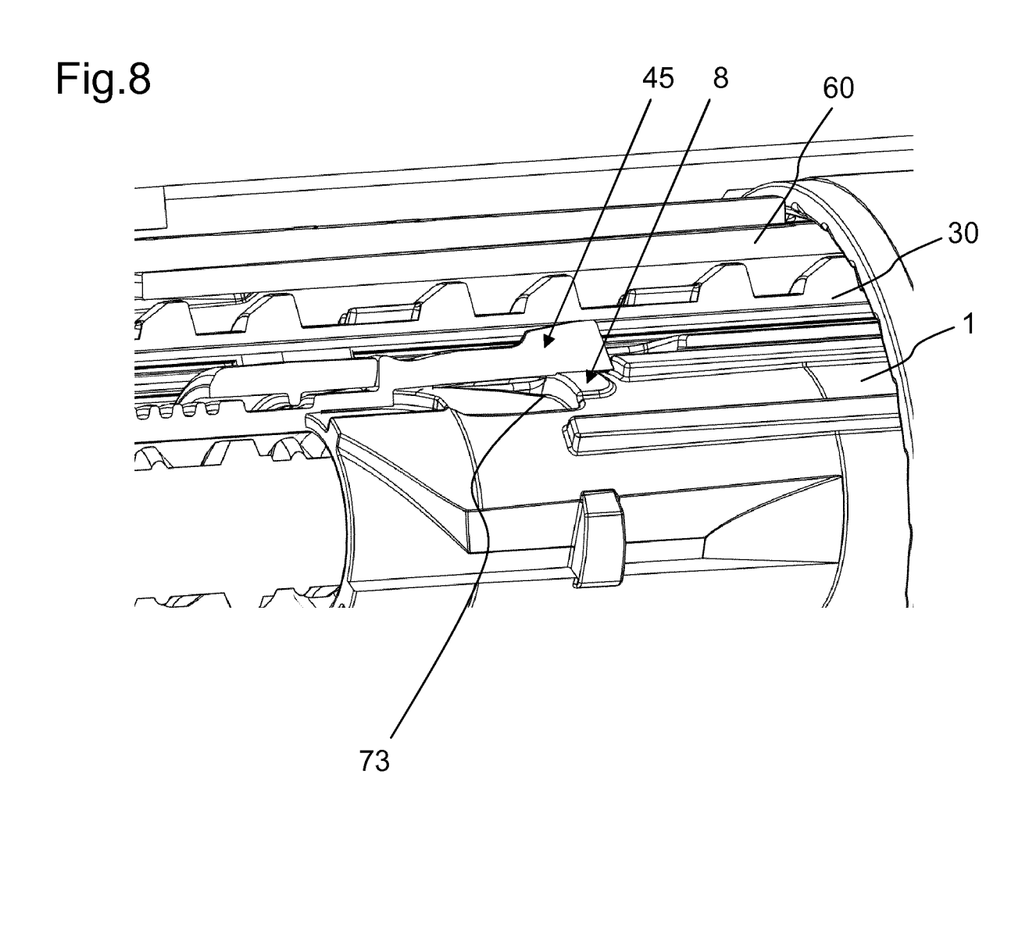
FIG. 8 shows a partial perspective view of inner components of the drug delivery device similar to FIG. 5.

Upon pressing the activation member 1 the clutch features 61, 7 disengage as shown in FIG. 7 and relative rotation between the indication member 60 and the activation member 1 is possible. In all conditions, the driver 40 and the activation member 1 are rotationally locked together. Thus, with the clutch 61, 7 disengaged (activation member 1 pushed in), the indication member 60 is free to rotate with respect to the activation member 1. In this condition, the activation member 1, the driver 40 and the indication member 60 are also axially coupled. A small amount of relative axial movement between the activation member 1 and the driver 40 is permitted and this results in the pocket or recess 73 being shifted relative to the protrusion 45. This is shown in FIG. 8. Thus, the protrusion 45 is prevented from flexing inwards because the protrusion 45 rests on a non-recessed area 8 of activation member 1 (cf. FIG. 8). In this condition, the driver 40 and the activation member 1 are rotationally constrained to the inner body 20, thus preventing any rotation relative to the housing 11.

With the desired dose dialled, the activation member 1 can be depressed and the piston rod 30 driven forward to dispense drug from the cartridge 80. The interaction of mating threads between the piston rod 30, driver 40 and inner body 20 delivers a mechanical advantage of, e.g., 2:1.

When the activation member 1 is in the initial position, the protruding distance Dp is preferably less than the axial length of dose setting member 70 (cf. FIG. 3).

FIG. 9 shows a proximal end of an alternative embodiment of the drug delivery device 100. According to this embodiment, the dose setting member 70 comprises a circular cross-section which decreases at least over a certain axial distance with increasing distance from a proximal end face of the dose setting member 70. In the embodiment depicted in FIG. 9, the drug delivery device 100 is in an initial state, comparable to the FIG. 3, wherein the protruding distance is zero. However, the protruding distance may also deviate from zero by certain constructional tolerances. Preferably, the protruding distance is smaller than 2 mm.

Figure 10:
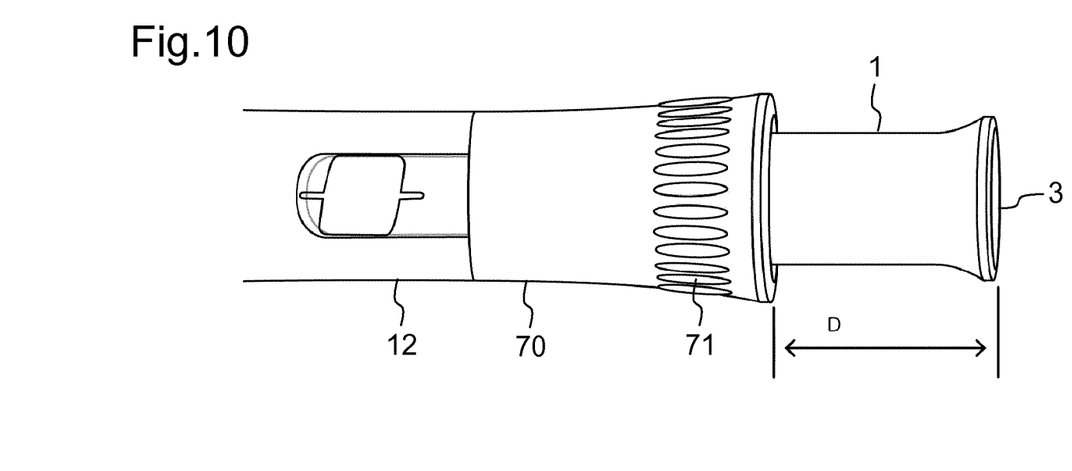
FIG. 10 shows a side view of a proximal end of the drug delivery device according to the embodiment shown in FIG. 9, wherein a dose is set.

In FIG. 10, and as compared to FIG. 9, the dose setting member 70 is in a dose set position, e.g. in a position, wherein a maximum dose of drug, is set. The distance D by which the activation member 1 protrudes beyond the proximal end of the housing is, e.g., the maximum axial distance by which the activation member 1 can be moved proximally with respect to the dose setting member 70 during a dose setting operation.

The maximum settable dose of the device may be 120 units or another quantity of drug, for example.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Activation member
2 Proximal end section (dose setting member)
3 Activation face
5 Gripping face
6 Arrow (counter clockwise)
7 Clutch feature (activation member)
8 Area
9 Proximal end section (activation member)
11 Housing
12 Housing part
13 Opaque layer
14 Window
16 Distal end
17 Proximal end
20 Inner housing, inner body
21 External thread (inner body)
22 Spline (inner body)
30 Piston rod
31 Bearing
40 Drive member, driver
41 External thread (drive member)
45 Protrusion
50 Nut, last dose member
60 Indication member
61 Clutch feature (indication member)
70 Dose setting member,
71 Gripping feature
72 Sleeve-like part
73 Recess
80 Cartridge
83 Annular metal band
82 Piston, bung
90 Cap
100 Drug delivery device
D Axial distance
Dp Protruding distance

The invention claimed is:

1. An assembly for a drug delivery device, the assembly comprising:
   a dose setting member configured to be moved by a user from an initial position to a dose set position to set a dose,
   a main housing part, wherein the dose setting member and the main housing part are connected to form a housing of the assembly, the housing having a proximal end and a distal end, and
   an activation member which is coupled to the dose setting member to convert a rotation of the dose setting member with respect to the housing into a proximal movement of the activation member with respect to the dose setting member when the dose setting member is moved from the initial position to the dose set position, the activation member having a proximal end section extending from an activation face of the activation member, the activation face being configured for an interaction with the user,
   wherein the assembly is configured such that, in the initial position of the dose setting member, the proximal end section of the activation member is fully received in the housing or slightly protrudes by a protruding distance beyond the proximal end of the housing,
   wherein the activation member is coupled to a piston rod of the assembly such that the activation member is moved proximally with respect to the dose setting member when the dose setting member is moved from the initial position to the dose set position, and
   wherein the assembly is further configured such that, when the set dose is increased, an axial extension of the drug delivery device also increases in proportion as the activation member moves proximally with respect to the dose setting member.

2. The assembly according to claim 1, wherein the protruding distance is less than a length of the dose setting member.

3. The assembly according to claim 1, wherein the protruding distance is less than or equal to 20% of a maximum distance by which the activation member can be moved proximally with respect to the dose setting member during a dose setting operation.

4. The assembly according to claim 1, wherein the protruding distance is zero.

5. The assembly according to claim 1, wherein the dose setting member is axially secured to but rotatable with respect to the main housing part.

6. The assembly according to claim 1, wherein the dose setting member defines the proximal end of the housing.

7. The assembly according to claim 1, wherein, in the initial position of the dose setting member, the proximal end of the housing ends flush with the activation face of the activation member.

8. The assembly according to claim 1, wherein, during setting of the dose, a length of the activation member protruding beyond the proximal end of the housing increases.

9. The assembly according to claim 1, wherein at least a portion of the dose setting member has a non-circular cross section.

10. The assembly according to claim 1, wherein the activation face of the activation member is curved.

11. The assembly according to claim 1, wherein the activation member is rotationally locked with respect to the dose setting member.

12. The assembly according to claim 1, wherein an axial movement of the activation member during setting of a dose is proportional to a number of units indicated by an indication mechanism of the assembly.

13. The assembly according to claim 1, wherein the activation member is coupled to the piston rod of the assembly via a drive member of the assembly.

14. A drug delivery device comprising:
   a dose setting member configured to be moved by a user from an initial position to a dose set position to set a dose,
   a main housing part connected to the dose setting member to form a housing of the drug delivery device, the housing having a proximal end and a distal end,
   an activation member which is coupled to the dose setting member to convert a rotation of the dose setting member with respect to the housing into a proximal movement of the activation member with respect to the dose setting member when the dose setting member is moved from the initial position to the dose set position, the activation member having a proximal end section extending from an activation face of the activation member, the activation face being configured for an interaction with the user, and
   a drive mechanism disposed within the housing and configured to expel a drug from the drug delivery device when activated,
   wherein the drug delivery device is configured such that, in the initial position of the dose setting member, the proximal end section is fully received in the housing or slightly protrudes by a protruding distance beyond the proximal end of the housing,
   wherein the activation member is coupled to a piston rod of the drive mechanism such that the activation member is moved proximally with respect to the dose setting member when the dose setting member is moved from the initial position to the dose set position, and
   wherein the drug delivery device is further configured such that, when the set dose is increased, an axial extension of the drug delivery device also increases in proportion as the activation member moves proximally with respect to the dose setting member.

15. The drug delivery device according to claim 14, wherein the piston rod is a symmetrical piston rod.

16. The drug delivery device according to claim 14, wherein the protruding distance is less than a length of the dose setting member.

17. The drug delivery device according to claim 14, wherein the protruding distance is less than or equal to 20% of a maximum distance by which the activation member can be moved proximally with respect to the dose setting member during a dose setting operation.

18. The drug delivery device according to claim 14, wherein the protruding distance is zero.

19. The drug delivery device according to claim 14, wherein the activation member is rotationally locked with respect to the dose setting member.

20. The drug delivery device according to claim 14, wherein an axial movement of the activation member during setting of a dose is proportional to a number of units indicated by an indication mechanism of the drug delivery device.

21. The drug delivery device according to claim 14, wherein the activation member is coupled to the piston rod of the drive mechanism via a drive member of the drive mechanism.

\* \* \* \* \*

UNITED STATES PATENT AND TRADEMARK OFFICE
CERTIFICATE OF CORRECTION

PATENT NO. : 10,500,346 B2
APPLICATION NO. : 14/915440
DATED : December 10, 2019
INVENTOR(S) : Michael Bainton and David Aubrey Plumptre Page 1 of 1

It is certified that error appears in the above-identified patent and that said Letters Patent is hereby corrected as shown below:

On the Title Page

Item (57), Column 2, Line 3 under "ABSTRACT", delete "sett" and insert -- setting --

Signed and Sealed this
Eleventh Day of February, 2020

Andrei Iancu
*Director of the United States Patent and Trademark Office*